United States Patent
Metwally (12)

(10) Patent No.: US 6,490,747 B1
(45) Date of Patent: Dec. 10, 2002

(54) ELECTRIC TOOTHBRUSH ATTACHMENT

(76) Inventor: Maged Metwally, P.O. Box 2650, Stuart, FL (US) 34995

( * ) Notice: Subject to any disclaimer, the term of this patent is extended or adjusted under 35 U.S.C. 154(b) by 0 days.

(21) Appl. No.: 09/528,570

(22) Filed: Mar. 20, 2000

(51) Int. Cl.[7] ............................. A46B 9/04; A46B 13/02
(52) U.S. Cl. ......................... 15/22.1; 15/28; 15/207.2; 15/167.1; 132/322; 132/329
(58) Field of Search ................. 15/22.1, 207.2, 15/167.1, 23, 28; 132/321, 322, 329

(56) References Cited

U.S. PATENT DOCUMENTS

| | | | |
|---|---|---|---|
| 200,736 A | * | 2/1878 | Lee |
| 792,471 A | * | 6/1905 | Smith |
| 1,979,240 A | * | 11/1934 | Adelmann |
| 1,982,285 A | * | 11/1934 | Bronner |
| 2,251,853 A | * | 8/1941 | Pandiyan |
| 4,344,202 A | * | 8/1982 | Hayat |
| 4,462,136 A | * | 7/1984 | Nakao |
| 4,886,078 A | * | 12/1989 | Shiffman |
| 5,009,886 A | * | 4/1991 | Ahmad |
| 5,069,621 A | * | 12/1991 | Paradis |
| 5,393,229 A | * | 2/1995 | Ram |
| 5,613,258 A | | 3/1997 | Hilfinger et al. |
| 5,652,990 A | | 8/1997 | Dreisen et al. |
| 5,862,558 A | | 1/1999 | Hilfinger et al. |
| 5,867,856 A | | 2/1999 | Herzog |
| 5,939,049 A | | 8/1999 | Miller et al. |

FOREIGN PATENT DOCUMENTS

DE        24 28 780        * 1/1976

* cited by examiner

*Primary Examiner*—Randall E. Chin
(74) *Attorney, Agent, or Firm*—McHale & Slavin

(57) ABSTRACT

A electric toothbrush attachment consisting of a miswaak element. The attachment is positioned to rotate at ninety degrees from the rotation of the arm. This motion results in a circular movement of the brush element against the surfaces of the teeth. The brush element is mounted on a disk which rotates in response to rotation of arm. The brush element may be fixed to the disk by adhesive. The brush element has a conical shaped end is left in water to provide soft bristles upon use.

5 Claims, 2 Drawing Sheets

ELECTRIC TOOTHBRUSH ATTACHMENT

FIELD OF THE INVENTION

This invention relates to mechanized toothbrushes, in general, and specifically to the structure and materials of the replaceable brush element.

BACKGROUND OF THE INVENTION

One of the tenets of Islam is the miswaak or the use of the miswaak. This has to do with the cleansing of the teeth and mouth, including the proper ways to do so and the proper materials for use in the exercise. In some uses of the term, miswaak refers to the specific implement used for cleaning the teeth.

Miswaak can be twigs of certain trees that are used to maintain oral hygiene. Almost any type of tree may be used as long as the trees are not harmful or poisonous. Certain woods are not permitted to be used for miswaak, such as the Pomegranate, Bamboo, Raihaan, or Chambelie. Recommended woods include the Peelo tree, known botanically as azadirachta, Zaitoon or Olive tree, Bitam, Walnut or any bitter tree.

These twigs are cut to a particular size, cleaned and dried. The wood fibers extend along the length of the prepared twig.

The twigs are manually placed in the mouth and rubbed against the teeth and gums. As the saliva penetrates the wood, the end of the twig, or miswaak, becomes softened and the individual fibers separate. This moistened fibrous end performs or acts as the bristles of a toothbrush. The softening of the wood also releases the natural oils within the twig further contributing to the efficacy of the mechanical brushing.

Mechanized toothbrushes, sometimes referred to as electric toothbrushes, are well known in the toothbrush art. There are mechanized toothbrushes that have bristles mounted perpendicularly in an annular disk. The disk has a powered rotation in the same plane as the diameter of the disk. Other rotary brushes have an elongated shaft with the bristles mounted radially along the shaft. Some toothbrushes have a powered shaft that reciprocates in a plane normal to the length of the bristles mounted on the shaft.

Other mechanized toothbrushes have bristles with one end mounted in a shaft that oscillates through an arc. The radius of the arc is parallel with the length of the bristles.

Regardless of the particular movement of the bristles of the various toothbrushes, the bristles receive the most wear and must be replaced more often than the other elements of the mechanized toothbrush. Usually, the bristles are made of a material that is stiff, durable and resilient for long wear.

Ahmed et al, U.S. Pat. No. 5,009,886, teaches the use of miswaak in a dentifrice. The dentifrice may be in the form of a tooth powder, a gel or a rinse.

Miller et al, U.S. Pat. No. 5,939,049, discloses a chewing stick made of natural fibers. The stick may be reused, as desired.

Driesen et al, U.S. Pat. No. 5,652,990, illustrates a typical electric rotary toothbrush having a disk with one end of elongated bristles mounted on the disk. The disk rotates in the plane of the disk. Hilfinger et al, U.S. Pat. No. 5,613,258, shows a rotary toothbrush with the bristles mounted in an elongated shaft.

Herzog, U.S. Pat. No. 5,867,856, discloses an electric toothbrush which has an oscillating motion and a rotary motion imparted to the bristles. While Hilfinger et al, U.S. Pat. No. 5,862,558, shows a reciprocating/rotating bristle action.

All of the prior art devices are of modular construction so that the element carrying the bristles, regardless of its complexity, is replaceable. The bristles of these devices are usually made of a plastic composition.

SUMMARY OF THE INVENTION

The instant invention is an attachment to an electric toothbrush having a handle portion and a rotary arm. The brush element is constructed from the miswaak plant and is positioned to rotate at ninety degrees from the rotation of the arm. This motion results in a circular movement of the brush element against the surfaces of the teeth.

The brush element or miswaak is made from a piece of a twig from a nonpoisonous tree and mounted on a disk which rotates in response to rotation of arm. The brush element may be fixed to the disk by adhesive of a waterproof consistency allowing the brush element to remain in a soaking container between uses. The end of the brush element connected with the disk may be planar or roughened. The surface of the disk contacting the roughened brush end may be similarly shaped to form a cooperating keyed connection. The working end of the brush element has a conical depression.

Accordingly, it is an objective of the instant invention to provide a replaceable brush element for mechanized toothbrushes with the brushing element in the form of a solid block of natural material which is composed of natural fibers.

It is a further objective of the instant invention to provide a brush element for electric toothbrushes with a solid block of materials that contribute to the efficacy of the brushing action. In use, the solid mass breaks down into fibrous material for more intimate contact with the teeth and releases the natural oils contained in the mass.

It is yet another objective of the instant invention to teach the use of a mounted piece of wood in a brush element of a mechanized toothbrush. The wood can come from the Peelo tree, known botanically as azadirachta or salvadora persica.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
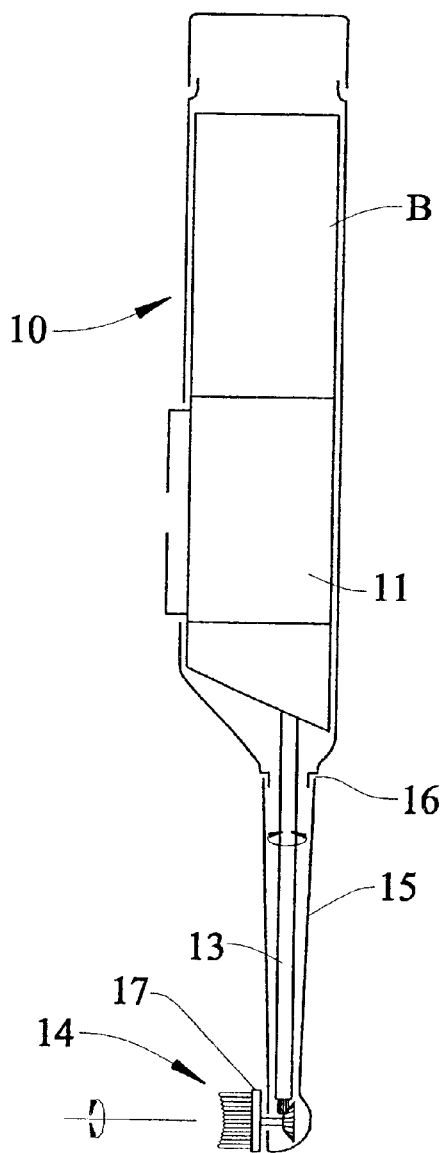
FIG. 1 is a cross section of an electric toothbrush with a solid block brush element.

As shown in FIG. 1, an electric toothbrush 10 has a handle portion 11 containing a battery B, a motor 12 and a rotary arm 13. The battery B, motor 12 and rotary arm 13 provide electromechanical power to move the arm in a repetitious cycle. The arm 13 extends beyond the handle portion and carries the brush element 14. The arm 13 and the housing 15 are releasably engaged at the joint 16 with the handle portion 11. The entire assembly of the arm 13, the housing 15 and the brush element 14 are replaceable in normal usage.

As shown, the brush element rotates at ninety degrees from the rotation of the arm 13. This motion results in a circular movement of the brush element against the surfaces of the teeth. In the event of a power failure, for any reason, the electric toothbrush may be used as a manual brush.

The brush element or miswaak 14 is made from a piece of a twig from a nonpoisonous tree. The brush element is mounted on a disk 17 which rotates in response to rotation of arm 13. The brush element 14 may be fixed to the disk 17 by adhesive 18. The adhesive may be waterproof and saturate the end of the brush element to provide a stable connection between the brush element 14 and the disk 17 during use. The disk 17 may be made of metal or plastic.

Figure 3:
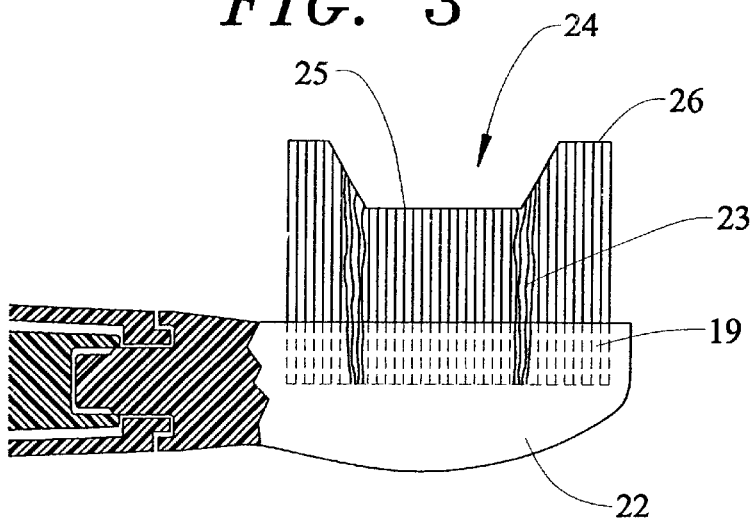
FIG. 3 is an cross section of a reciprocating electric toothbrush with the solid block of material showing fiber direction.

In the event the disk 17 is made of plastic, the disk may be molded in one piece with the brush element 14 forming a unitary piece. As shown in FIG. 3, the plastic composition of the reciprocating element 22 is molded about the end 19 of the brush element forming a unitary piece. Other connections may be made between the disk and the brush element, such as staples, screws and nails.

Figure 2:
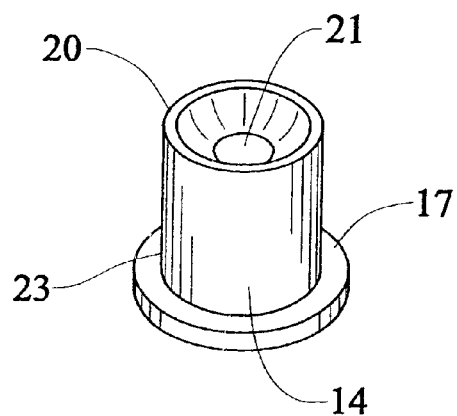
FIG. 2 is an elevation view of a solid mass used in electric toothbrushes shown in FIG. 1.

As shown in FIG. 2, the brush element 14 is a cylindrical piece of wood. The end of the brush element connected with the disk 17 may be planar or roughened (not shown). The surface of the disk contacting the roughened brush end may be similarly shaped (not shown)to form a cooperating keyed connection.

The working end of the brush element 14 has a conical depression. The upper edge 20 of the depression forms a circular surface which initially engages the teeth. The smaller end surface 21 forms an end wall of the depression. The internal wood fibers 23 extend through the brush element 14 from the disk 17 toward the depression.

In FIG. 3, the reciprocating element 22 may be formed as an elliptical section rather than as a cylinder. The brush element 14 may also be in the form of a rectangular section. In either case, the brush element 14 has a central depression 24. The depression 24 has an end wall 25 and side walls that slope outwardly toward a larger base surface 26.

Figure 4:
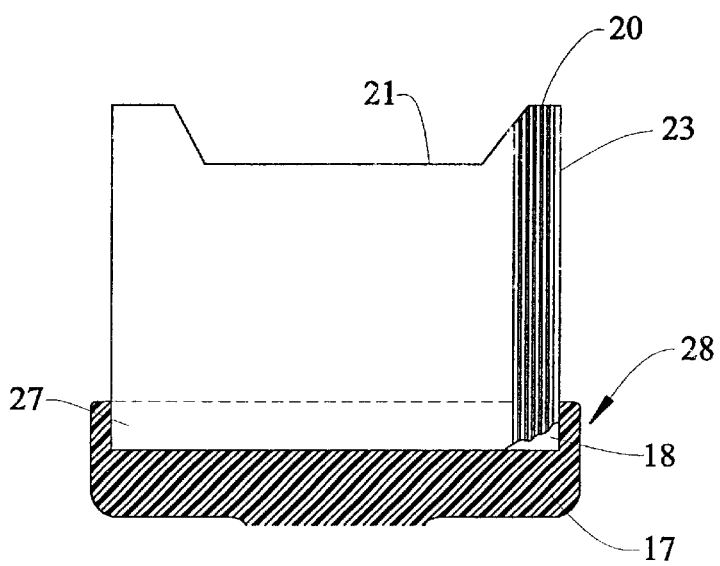
FIG. 4 is a cross section of a rotary electric toothbrush with the solid block of material showing fiber direction.

FIG. 4 shows the support end 27 of brush element 14 received in a well formed by an upstanding shoulder 28 on the disk 17. The coextensive surfaces of the well and the brush element may be coated with adhesive or other fixing agent. The sidewalls of the well may be penetrated by other fasteners (not shown) extending into the support end 27 of the brush element.

Figure 5:
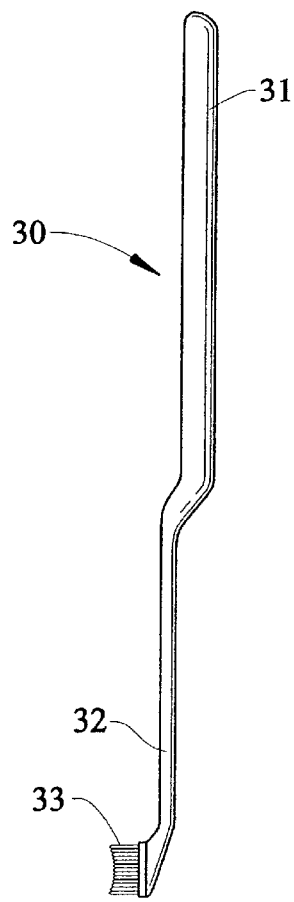
FIG. 5 is an elevation of a manual toothbrush with a solid block brush element.

FIG. 5 illustrates the use of the solid block of wood or miswaak in a manual toothbrush. In some situations and locations, electric power and/or batteries may not be available. Certainly, the electric toothbrushes disclosed here can be used manually in those situations. However, a less complex toothbrush 30 with a handle 31 and an arm 32 extending from the handle may also be provided. One end of the arm 32 attaches to the handle 31 and the other end of the arm carries the solid block of wood brush element 33. The fibers of the solid block of wood extend perpendicular to the length of the arm.

The arm and handle may be made of a plastic composition molded as one piece or several elements connected together to form an integral unit. The wood brush element 33 may be connected to the arm by molding, heat shrink, adhesive, or mechanical fasteners.

The miswaak can be attached by adhesive, plastic shrink, or a coupling attachment. The shape of the brush includes a cavity to allow bristles to form. Thus, in operation, the longer the brush is used the softer the bristles become. Further, the device allows for soaking of the brush allowing water to maintain the bristles in a softened state.

The actual attachment to an electric toothbrush can be made to accommodate the particular manufacturer of the toothbrush. For instance, a replacement brush that clips on can have a replacement of the instant invention to match the mounting mechanism. Further, various handles can be modified to attach the miswaak brush, the variations of which are basic to design and incorporated herein. Without electric power, any of the electric toothbrushes may be operated manually. The It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. In a toothbrush having a handle portion, an arm connected at one end to said handle portion and carrying a solid brush element on the other end, said solid brush element composed of wood fibers, said solid brush element oriented on said arm with said wood fibers normal to said arm, wherein said toothbrush is an electric toothbrush, said handle portion containing an electro mechanical power means for imparting a repetitious movement, said power means connected through said arm to said solid brush element, and said power means translating said repetitious movement to said solid brush element whereby the movement of said solid brush element against the teeth results in separation of said wood fibers and the formation wood fiber bristles.

2. In an electric toothbrush as claimed in claim 1, said solid brush element having a base and a working surface, said base connected to said arm, said wood fibers of said solid element extending from said base to said working surface.

3. In an electric toothbrush as claimed in claim 2, said solid brush element having a depression in said working surface.

4. In an electric toothbrush as claimed in claim 3, said base of said solid brush element adhered to said arm.

5. In an electric toothbrush as claimed in claim 3, said other end of said arm having a plastic portion, said base of said solid brush element molded into said plastic of said arm.

* * * * *